US009149831B2

(12) United States Patent
Plans et al.

(10) Patent No.: US 9,149,831 B2
(45) Date of Patent: Oct. 6, 2015

(54) STENT HOLDING FIXTURES

(71) Applicant: Abbott Cardiovascular Systems Inc., Santa Clara, CA (US)

(72) Inventors: Isaac Rodriguez-Mejia Plans, Galway (IE); Javier Palomar Moreno, Galway (IE); Tomás Madden, Galway (IE); David O'Neill, Galway (IE); Victoria May Gong, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/871,952

(22) Filed: Apr. 26, 2013

(65) Prior Publication Data

US 2013/0241132 A1 Sep. 19, 2013

Related U.S. Application Data

(62) Division of application No. 11/781,181, filed on Jul. 20, 2007, now Pat. No. 8,453,598.

(60) Provisional application No. 60/807,897, filed on Jul. 20, 2006.

(51) Int. Cl.
*B05C 13/02* (2006.01)
*B05B 13/02* (2006.01)
*B05B 13/04* (2006.01)
*B05B 12/04* (2006.01)
*A61F 2/82* (2013.01)

(52) U.S. Cl.
CPC ............... *B05C 13/025* (2013.01); *B05B 12/04* (2013.01); *B05B 13/0235* (2013.01); *B05B 13/0442* (2013.01); *A61F 2/82* (2013.01)

(58) Field of Classification Search
None
See application file for complete search history.

(56) References Cited

U.S. PATENT DOCUMENTS

| 6,723,373 | B1 | 4/2004 | Narayanan et al. |
| 6,818,063 | B1 * | 11/2004 | Kerrigan ..................... 118/500 |
| 6,957,152 | B1 | 10/2005 | Esbeck |
| 7,232,490 | B1 * | 6/2007 | Hossainy ..................... 118/320 |
| 2003/0113439 | A1 * | 6/2003 | Pacetti et al. .............. 427/2.24 |
| 2004/0013792 | A1 * | 1/2004 | Epstein et al. ............. 427/2.24 |
| 2005/0149162 | A1 | 7/2005 | Tenhuisen et al. |
| 2005/0166841 | A1 * | 8/2005 | Robida .......................... 118/500 |
| 2007/0112381 | A1 | 5/2007 | Figulla et al. |
| 2007/0259100 | A1 * | 11/2007 | Guerriero et al. ........... 427/2.24 |

* cited by examiner

*Primary Examiner* — Dah-Wei D Yuan
*Assistant Examiner* — Jethro M Pence
(74) *Attorney, Agent, or Firm* — Squire Patton Boggs (US) LLP

(57) ABSTRACT

Disclosed are stent holding devices having a support mandrel and one or more stent retaining fixtures disposed on the mandrel. The retaining fixture may include a character identifier to facilitate tracking a stent mounted on the holding device. The retaining fixture may include a conical protrusion and a conical recess to allow any number of retaining fixtures to engage each other and be stacked on the mandrel. The retaining fixture may include a tubular member having a spiral cut that enables the diameter of the tubular member to be adjusted to allow for a frictional fit on the mandrel. The retaining fixture may have a Z-shaped or T-shaped structure configured to retain a stent. The stent retaining fixture may also have a filament for retaining a stent.

11 Claims, 7 Drawing Sheets

STENT HOLDING FIXTURES

This is a divisional application of U.S. application Ser. No. 11/781,181 filed on Jul. 20, 2007 which claims the benefit of U.S. Provisional Application No. 60/807,897, filed Jul. 20, 2006, the entire contents of both being incorporated herein by reference.

BACKGROUND OF THE INVENTION

1. Field of the Invention

The present invention relates generally to supports for holding a stent, and more particularly, but not exclusively, relates to devices for holding a stent during manufacturing processing such as electropolishing or spray coating the stent with a beneficial agent or other coating.

2. Background of the Invention

Stents, grafts and a variety of other endoprosthesis are well known and used in interventional procedures, such as for treating aneurysms, for lining or repairing vessel walls, for filtering or controlling fluid flow, and for expanding or scaffolding occluded or collapsed vessels. Such endoprosthesis can be delivered and used in virtually any accessible body lumen of a human or animal, and can be deployed by any variety of recognized means. One recognized indication of endoprosthesis, such as stents, is for the treatment of aetherosclerotic stenosis in blood vessels. For example, after a patient undergoes a percutaneous transluminal coronary angioplasty or similar interventional procedure, an endoprosthesis, such as a stent, is often deployed at the treatment site to improve the results of the medical procedure and to reduce the likelihood of restenosis. The endoprosthesis is configured to scaffold or support the treated blood vessel; if desired, the endoprosthesis can also be loaded with beneficial agent so as to act as a delivery platform to reduce restenosis or the like.

Generally there are two distinct types of endoprosthesis, balloon expandable and self-expanding endoprosthesis. A balloon expandable endoprosthesis is generally constructed of materials such as stainless steel, cobalt chromium or some blend thereof, wherein the stent is crimped onto a balloon for delivery into a vessel or artery. The stent may be plastically deformed when crimped onto the balloon and then plastically deformed when the balloon is expanded to deploy the prosthesis. Generally balloon-expandable stents are cut from tubes and then undergo various manufacturing processes to become a finished product.

Self-expanding stents are generally fabricated from metals having superelastic properties, wherein the stent pattern is cut into a tube, wherein the cut tube undergoes a series of manufacturing steps to become a finished product.

Typically after the stent pattern has been cut into the wall of the tubing to form the stent, the stent is blasted with media to remove burs, slag and other manufacturing byproducts. After blasting, the stents are generally electropolished to create a smooth surface along the length of the stent as well as along the cut edges of the stent. During the electropolishing step, the stents are generally mounted on a mandrel and submerged in a chemical bath to perform the polishing process as described in U.S. patent application Ser. No. 11/370,660 (U.S. Pat. No. 8,038,803), entitled "Method of Descaling Metallic Devices," the entirety of which is herein incorporated by reference.

After having been polished, generally the stents are ready for use and mounted on their respective delivery systems. If it is desired, the stents may be coated with a beneficial agent for release within a vessel or artery after delivery of the endoprosthesis therein. If the stent is to be coated with a coating such as a beneficial agent this is generally done before the stent is mounted onto a delivery system.

There are various methods for applying a coating to an endoprosthesis. The most common method is to mount the endoprosthesis on a mandrel and spray a coating onto the surface of the endoprosthesis. It is preferred that all surfaces of the endoprosthesis are covered, through this is often difficult because the mandrel used to hold the endoprosthesis results in a discontinuity in the surface coating which could lead to coating failure or having the coating flake off the endoprosthesis upon delivery.

Typically when a stent has a coating applied to it, the stent must be tracked during the manufacturing process for regulatory reasons. This tracking may be performed by using numbered vials to hold the stent, or a numbered board to hold the mandrels. As production numbers increase it may become difficult to properly track each individual stent during the manufacturing process, therefore there is a need for an improved method and/or device for tracking a stent during production. There is also a need for improved mandrel designs to retain an endoprosthesis during manufacturing and coating. The present invention satisfies these and other needs.

SUMMARY OF THE INVENTION

In accordance with the present invention, there is provided a stent holding device comprising a support mandrel sized to fit in a stent lumen, and a stent retaining element removably attached to the support mandrel, the stent retaining element including a character identifier.

In other aspects of the present invention, a stent holding device comprises a support mandrel sized to fit in a stent lumen, and a plurality of fixtures, each including a protruding surface that is sloped relative to a longitudinal axis of the support mandrel, at least one of the plurality of fixtures includes an aperture having a recess shaped to receive the protruding surface of another one of the plurality of fixtures.

In further aspects of the present invention, the support mandrel extends into and frictionally engages the aperture of the at least one of the plurality of fixtures.

In yet other aspects of the present invention, a stent holding device comprises a mandrel including a segment sized to fit in a stent lumen, and a fixture removably attached to the mandrel, the fixture including a loop segment defining an inner diameter of the fixture, the inner diameter expandable from a first size, when the fixture is removed from the mandrel, to a second size, when the fixture is attached to the mandrel, the first size less than an outer diameter of the mandrel, the second size allowing for a friction fit between the loop segment and the mandrel.

In detailed aspects, the fixture includes a plurality of interconnected loop segments wrapped around the support mandrel.

In other aspects of the present invention, a stent holding apparatus comprises a first end region, a second end region spaced apart from the first end region, and a stent retaining assembly disposed at the first end region, the stent retaining assembly including two arms extending toward the second end region and a stent contacting member disposed between and attached to the two arms.

In further aspects, the stent holding apparatus comprises a second stent retaining assembly disposed at the second end region, the second stent retaining assembly including two arms extending toward the first end region and a stent contacting member disposed between and attached to the two arms of the second stent retaining assembly.

The stent contacting member is removably attached to the two arms in other aspects of the present invention.

In detailed aspects, the stent holding assembly is movable relative to the second end region and is coupled to a biasing device that urges the stent holding assembly to a selected position relative to the second end region.

The stent holding apparatus in further aspects comprises a rotational drive mechanism coupled to the stent retaining assembly such that the stent retaining assembly is rotated when the rotational drive mechanism is activated.

The stent holding apparatus in yet further aspects comprises a linear drive mechanism coupled to the stent retaining assembly such that the stent retaining assembly is translated linearly when the linear drive mechanism is activated.

In other aspects of the present invention, a stent holding apparatus comprises a support mandrel sized to fit in a stent lumen, and a Z-shaped fixture disposed on the support mandrel, the fixture including a first protruding portion extending in a radial direction away from the support mandrel and a second protruding portion extending in a different radial direction away from the support mandrel, the first and second protruding portions defining an outer diameter of the fixture, the outer diameter sized such that the first and second protruding portions are capable of engaging one or more luminal surfaces of the stent lumen.

In further aspects, the stent holding apparatus comprises another Z-shaped fixture disposed on the support mandrel, the fixture including a first protruding portion extending in a radial direction away from the support mandrel and a second protruding portion extending in a different radial direction away from the support mandrel, the first and second protruding portions defining an outer diameter of the fixture, the outer diameter sized such that the first and second protruding portions are capable of engaging one or more luminal surfaces of the stent lumen.

The features and advantages of the invention will be more readily understood from the following detailed description which should be read in conjunction with the accompanying drawings.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

In accordance with the present invention there is provided an exemplary embodiment of a stent holder or mandrel in accordance with the present invention. The stent holder in accordance with the present invention includes a support member and at least two stent receiving fixtures radially disposed about the support member, the receiving fixtures configured to retain a stent radially about the support member.

Figure 1A:
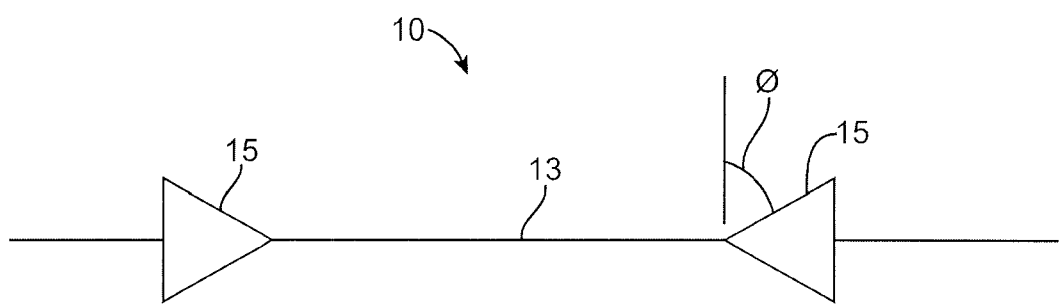
FIG. 1A is a plan view of stent holder showing two stent retaining fixtures disposed on and spaced apart along a support mandrel.

Referring now to FIG. 1A there is shown an exemplary embodiment of a stent holder in accordance with the present invention. As shown in FIG. 1A, the stent holder 10 includes a support mandrel 13 and two stent receiving fixtures 15 disposed upon the support mandrel 13.

The support mandrel 13 may be embodied in the form of a needle having a luer fitting on one end and a shaft, wherein the shaft of the support mandrel 13 may be constructed of metal or plastic. Preferably the material of which the support mandrel is constructed is relatively stiff and resistant to bending loads. Additionally, it is preferred that the support mandrel be constructed of a material which is chemically compatible with the coating to be applied to the stent. Also, it is desirable that the mandrel be resistant to extreme temperatures, either extreme cold or extremely hot temperatures without breaking.

The support mandrel 13 is constructed having a generally circular cross-sectional profile, though other cross-sectional geometries may be utilized. For example, a section of the support mandrel 13 disposed between the stent receiving fixtures 15 may be cylindrical wherein the sections of the support mandrel 13 under the stent receiving fixtures may have a different cross-sectional profile which may function as an indexing feature or locking feature for the stent receiving fixture. For example, the section of the support mandrel 13 configured to receive the stent receiving fixtures 15 may have a star-shaped cross-sectional profile (FIG. 5B) which would then index with a star-shaped aperture disposed through the stent receiving fixture 15. It is contemplated that other shapes may be utilized to perform the indexing as described herein and that the shapes described above are merely exemplary.

The stent receiving fixtures 15 as shown in FIG. 1A and described herein are constructed having an angle $\Phi$ with respect to the support mandrel 13. The angle $\Phi$ may range between about zero degrees to about seventy-five degrees.

The stent receiving fixtures 15 have an aperture disposed therethrough, wherein the aperture is sized to receive the support mandrel 13. As described above, the aperture and the support mandrel 13 may be shaped to provide an indexing feature. Additionally, the aperture disposed through the receiving fixtures 15 may be a tapered aperture, thereby causing the stent receiving fixtures to be frictionally engaged with the support mandrel 13.

The stent receiving fixtures 15 may be constructed of plastics such as Delrin, PVC, nylon or similar materials or constructed of metal such as stainless steel, aluminum, steel, titanium or other similar metals. Additionally, the surface finish of the fixtures may range from a rough surface to a highly polished surface.

In use, a first stent receiving fixture would be disposed upon the support mandrel, a stent would then be disposed radially about the support mandrel, the second stent receiving fixture is then placed onto the mandrel. The stent is supported on its ends by the sloped faces of each of the stent receiving fixtures. The support mandrel 13 may then be mounted into a spraying apparatus where the entire assembly may be rotated while being sprayed.

In some instances due to regulatory requirements it is necessary to track specific stents through the entire manufacturing process, wherein a serial number containing lot information about the beneficial agent is placed on the products finished label. The holder shown and described in FIG. 1A may include a laser engraved number on the luer, support member or on one or both of the stent receiving fixtures. Alternatively, the mandrel 10 may be disposed on a numbered board, wherein during manufacture, each mandrel would be placed and removed from the same location on the board each time.

Figure 1B:
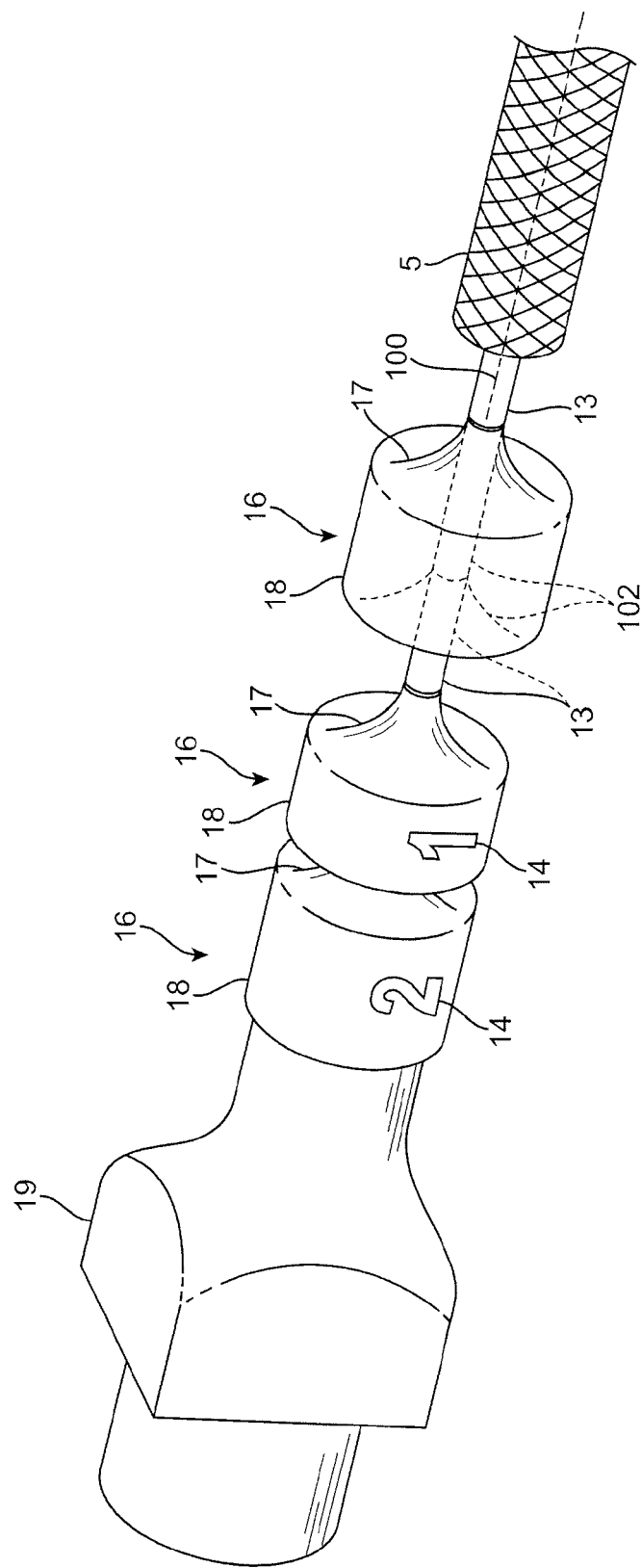
FIG. 1B is an exploded perspective view of a stent holding device showing a tracking feature removably attached to a support mandrel, the tracking feature including three stent retaining fixtures, two of the stent retaining fixtures having a numerical indicator.

Referring now to FIG. 1B there is shown an embodiment of a stent receiving fixture in accordance with the present invention. The stent receiving fixture of FIG. 1B is similar to that described above with regard to FIG. 1A, wherein the stent receiving fixture is configured to be radially disposed about a support member and configured at one end to hold a stent.

Figure 1C:
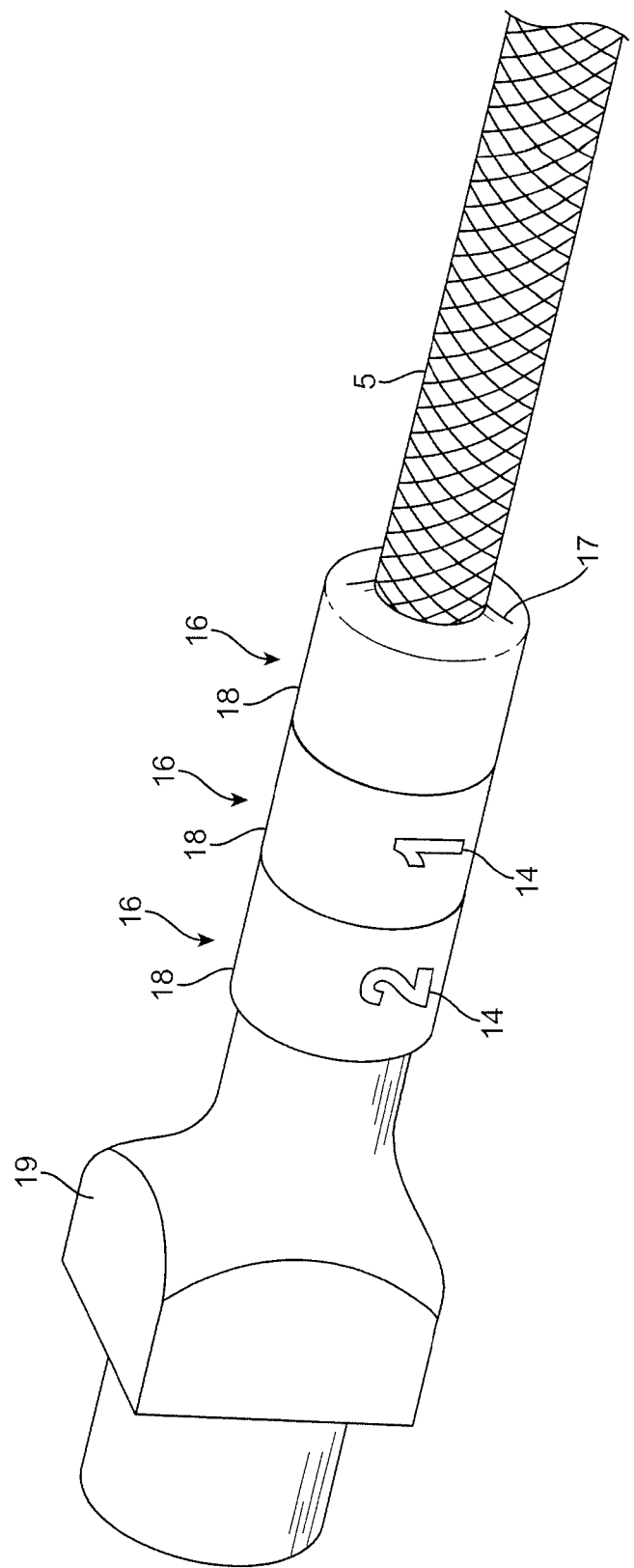
FIG. 1C is a perspective view of the stent holder of FIG. 1B showing the three stent retaining fixtures abutting each other and a stent disposed against a sloping surface of one of the stent retaining fixtures.

As shown in FIG. 1B, the stent receiving fixture 16 includes a shaped portion 17 and a body portion 18. The receiving fixture 16 may further include an identifier 14 which may be in the form of a number, letter, barcode, symbol, or other identifiable character. As shown in FIG. 1B, the shaped portion 17 of the fixture 16 is configured to either receive a stent 5 or be received by the body portion 18 of another fixture 16, wherein multiple fixtures 16 may be stacked together as shown in FIG. 1C. By stacking two or more fixtures 16, it is possible to assign distinct numbers to each holder assembly by utilizing fixtures with different identifiers.

The fixtures 16 may be constructed of materials such as those described above with regard to the mandrel of FIG. 1A.

Figure 1D:
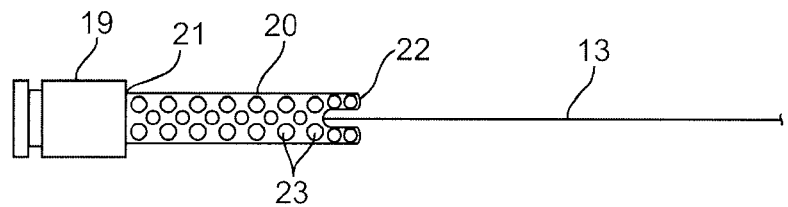
FIG. 1D is a plan view of a stent holding device showing a luer fitting abutting a fixture having a plurality of apertures, and a support mandrel extending from the fixture.

Referring now to FIG. 1D, there is shown another embodiment of a stent receiving fixture in accordance with the present invention. As shown in FIG. 1D, the stent fixture is configured to be received by a support mandrel in a manner similar to that described above. As shown, the stent fixture 20 has a first end 21 and a second end 22 wherein the first end is configured to abut a luer fitting 19 of the mandrel as shown. The second end 22 of the fixture 20 is shaped to receive a stent. The shaped end 22 of the fixture 20 is shaped such that it contacts the stent in a manner that limits the area of the contact between the stent and the fixture 20. Additionally as shown, the fixture 20 includes at least one aperture 23 formed in the body thereof and, preferably, a plurality of apertures 23 formed in the body of the fixture 20.

In use, the apertures 23 formed in the body of the fixture 20 allow for sprayed liquid coming in contact with the fixture 20 to pass through the apertures 23 of the fixture 20 instead of flowing around the fixture 20 and potentially onto the end of the stent being coated.

The fixture 20 may be formed of a metallic tubular member, wherein the fixture may be formed through laser cutting. It is also contemplated that the spacer be formed of the materials such as those described above.

Figure 1E:
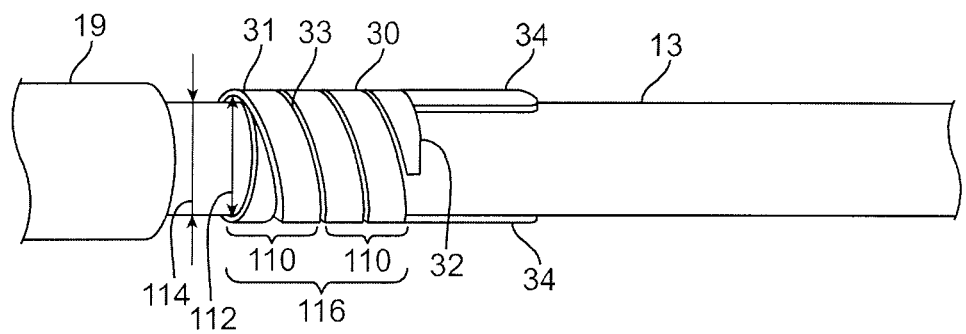
FIGS. 1E and 1F are perspective views of a stent holding device showing a tubular member in which a spiral cut extends from a first end to a second end of the tubular member.
Figure 1F:
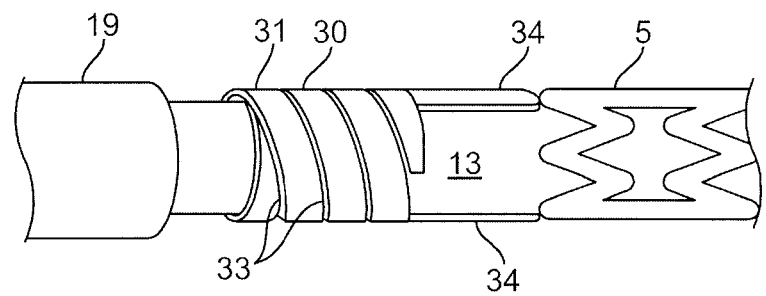

Referring now to FIGS. 1E and 1F, there is shown yet another embodiment of a holder in accordance with the present invention. The holder in accordance with FIGS. 1E and 1F comprises a generally tubular member having a first end and a second end, a plurality of cuts are formed within the tubular member thereby allowing the diameter of the tubular member to expand or contract.

As shown in FIG. 1E, the fixture 30 has a first end 31 and a second end 32, wherein the second end 32 includes at least one extension 34 extending from the second end. The extension 34 is configured to engage an end of a stent during a manufacturing process. The fixture 30 further includes a cut 33 formed therein. As shown in FIGS. 1E and 1F, the cut 33 is embodied as a spiral cut that wraps around the body and long the length of the fixture 30.

The fixture 30 is configured to be disposed radially about a support mandrel 13 as described above with regard to the mandrels in accordance with the present invention. As shown in FIG. 1E, the fixture 30 is radially disposed about the support mandrel 13, wherein the rotating the mandrel counterclockwise expands the diameter of the fixture 30 by increasing the spacing of the cut 33.

As shown in FIG. 1E, the fixture 30 is abutted at its first end 31 against a luer 19 on the support mandrel 13, and the extension 34 extending from the second end is abutted against a stent 5 that has been radially disposed about the support mandrel.

The fixture 30 as described above, can be expanded in diameter to fit tightly about the support mandrel 13 in order to position a stent 5 on the mandrel as shown in FIG. 1E. In addition to providing positive location of the stent, the extension(s) 34 are designed to form a space between the second end 32 of the body of the fixture and the stent 5 such that, as described above, any overspray from the coating process will not flow onto the end of the stent. Additionally, by using two fixtures, each disposed on ends of the stent, the fixture 30 can be positioned on the support mandrel 13 to provide a force to the stent 5 disposed therebetween. This force will retain the stent in a position on the mandrel 13 as desired by the user.

In a preferred embodiment, the diameter of the fixture 30 is less than that of the support mandrel 13. Therefore, the diameter of the fixture must be expanded in order to dispose the fixture over the support mandrel 13, thereby ensuring a friction fit between the fixture 30 and the support mandrel 13.

Figure 2:
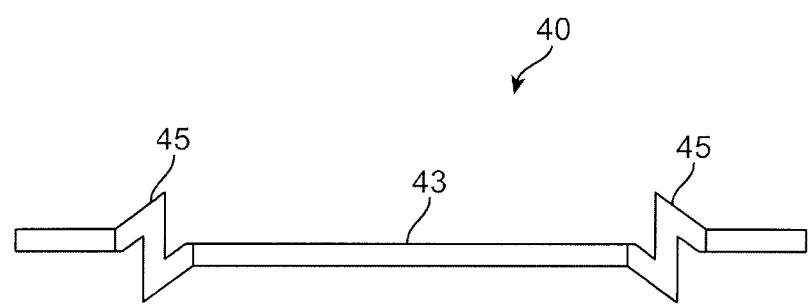
FIG. 2 is a plan view of a stent holding device showing two Z-shaped stent retaining fixtures spaced apart from each other on a support mandrel.
Figure 3:
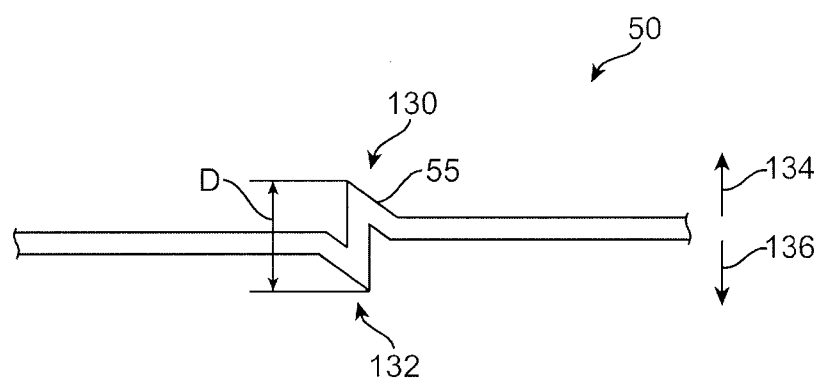
FIG. 3 is a plan view of a stent holding device showing a first protruding portion and a second protruding portion defining an outer diameter of a stent retaining fixture.
Figure 4:
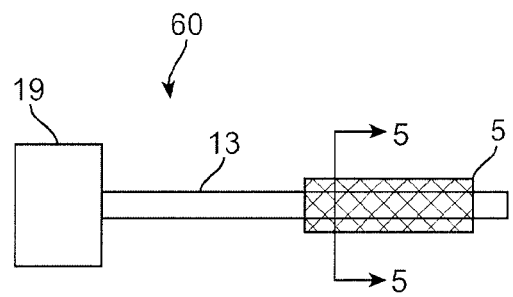
FIG. 4 is a plan view of a stent holding device showing a support mandrel and a luer fitting attached to one end of the support mandrel.

Referring now to FIGS. 2 and 3, there are shown other embodiments of a mandrel in accordance with the present invention. As shown in FIG. 2, the mandrel 40 comprises a support mandrel 43 having fixtures 45 integrally formed therein. The fixtures 45 in accordance with the mandrel 40 includes a Z-shaped fixture formed from the support mandrel 43, wherein the size of the fixtures and the spacing between the fixtures are selected so as to support a stent.

Referring now to FIG. 3, there is shown an embodiment of a mandrel 50 in accordance with the present invention. The mandrel 50 in accordance with FIG. 3 is similar to the mandrel 40 of FIG. 2, wherein as shown in FIG. 3, the mandrel 50 includes a fixture 55 formed of the support member 13, wherein the fixture 55 has a diameter D. The diameter D of the fixture 55 is sized to frictionally retain a stent when the mandrel 50 is placed within a lumen of the stent.

Referring now to FIGS. 4 and 5A-5E, there is shown exemplary embodiments of a mandrel design in accordance with the present invention. The mandrel 60 in accordance with the present invention includes a fitting 19 and a support mandrel 13 as described herein in accordance with the other mandrel embodiments. The fitting 19 may be a luer fitting or any other type of fitting that allows the mandrel to be received by another fixture such as an electropolishing fixture or a coating fixture.

Unlike the previously described mandrels, the mandrel in accordance with the present embodiment does not include a separate or integrated fixture as described above in connection with FIGS. 2 and 3. Instead, the support mandrel of the present embodiment is sized to retain a stent disposed thereabout as will be described in detail below with regard to FIGS. 5A through 5E.

Figure 5A:
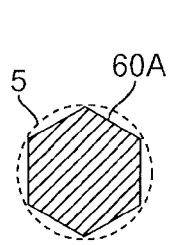
FIGS. 5A-5E are cross-sectional views of the support mandrel of the stent holding device of FIG. 4.

As shown in FIG. 5A, the support member 13 of the mandrel may have a multi-sided cross-sectional profile. The multi-sided cross-sectional profile may have four or more sides. As shown, when the mandrel 60A is disposed within a stent 5, the mandrel retains the stent at multiple contact points.

Figure 5B:
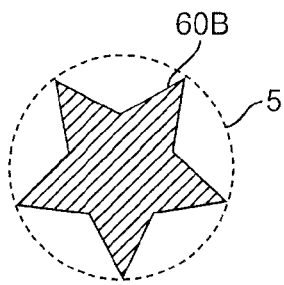

As shown in FIG. 5B, the support member 13 of the mandrel 60 may have a star-shaped cross-sectional profile. As shown, when the mandrel 60B is disposed within a stent 5, the mandrel retains the stent at multiple contact points.

Figure 5C:
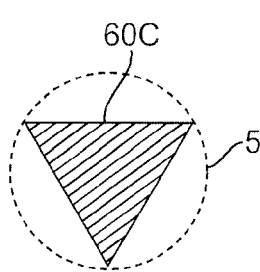

As shown in FIG. 5C, the support member 13 of the mandrel 60 may have a triangular cross-sectional profile. As shown, when the mandrel 60 is disposed within a stent 5, the mandrel retains the stent at multiple contact points.

Figure 5D:
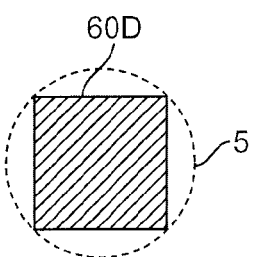

As shown in FIG. 5D, the support member 13 of the mandrel 60 may have a square cross-sectional profile. As shown, when the mandrel 60D is disposed within a stent 5, the mandrel retains the stent at multiple contact points.

Figure 5E:
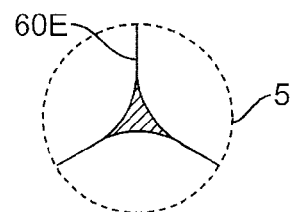

As shown in FIG. 5E, the support member 13 of the mandrel 60 may have a concave-triangular cross-sectional profile. As shown, when the mandrel 60E is disposed within a stent 5, the mandrel retains the stent at multiple contact points.

In accordance with each of the embodiments described above with regard to FIGS. 5A through 5E, it is contemplated that the support mandrel 13 in accordance with the mandrel 60 may have a continuous diameter along its entire length, or alternatively, the shapes shown and described above may be pattered along the length of the support mandrel 13. For example, the shapes may be disposed along the length of the mandrel in a screw-type fashion, disposed at intervals along the length of the support mandrel 13 or any combination thereof.

In other embodiments, the number of contact points can be more or less than the number of contact points shown in FIGS. 5A through 5E. For example, a six-point or seven-point star shape may be used to provide six or seven contact points, respectively. The number of contact points may also vary along the length of the mandrel 13. The number, size, shape, and configuration of contact points may be selected according to need. For example, a particular number, size, shape, and configuration of contact points may be needed to mask an inner surface area of a stent during a coating process. Additionally, a particular number, size, shape, and configuration of contact points may be needed to facilitate proper air mixing or drying.

Figure 6:
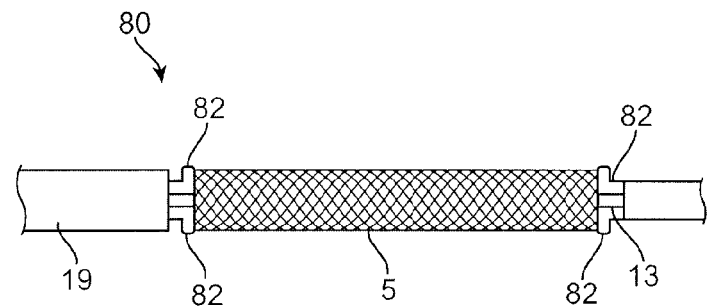
FIG. 6 is a plan view of a stent holder device showing a stent disposed between T-shaped stent retaining fixtures.

Referring now to FIG. 6, there is shown an embodiment of a mandrel in accordance with embodiments of the present invention. As shown in FIG. 6, the mandrel 80 includes a support member 13, a hub or luer 19, and at least one stent fixture 82. The stent fixture 82 as shown in FIG. 6 is configured to engage an end portion of a stent 5 as shown. The stent fixture 82 is preferably embodied as having a T-shape as shown.

Figure 7:
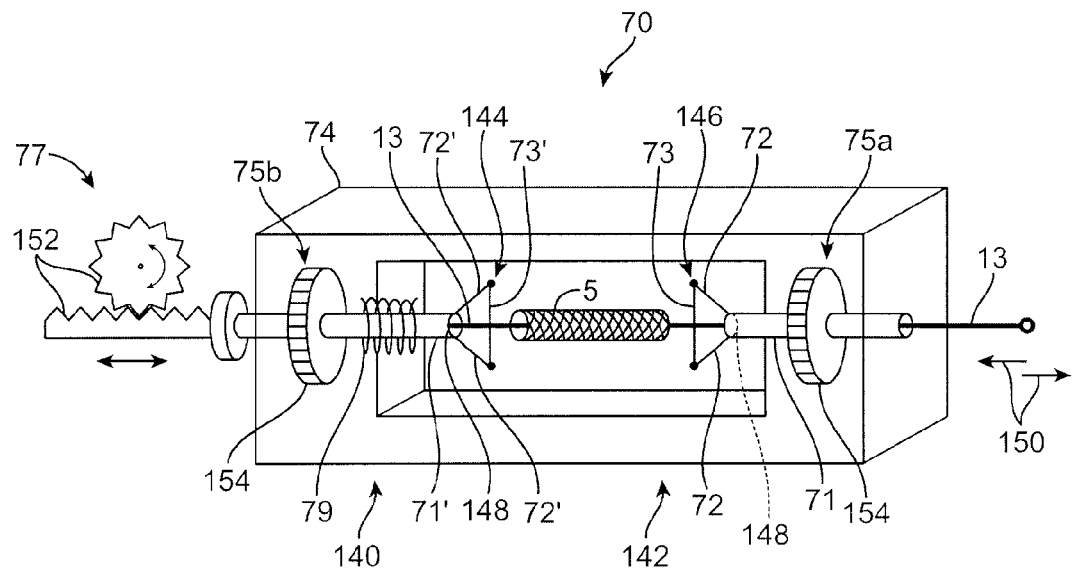
FIG. 7 is a perspective view of a stent holding apparatus showing two stent retaining fixtures spaced apart from each other, a support mandrel inserted into apertures formed into the two stent retaining fixtures, a biasing device and a linear drive mechanism coupled to the first stent retaining fixture, and a rotational drive mechanism coupled to the first and second stent retaining fixtures.

Referring now to FIG. 7, there is shown an mandrel 70 and associated fixturing in accordance with the embodiments of present invention. The mandrel and fixture shown in FIG. 7 includes a left fixture and a right fixture as well as a tension adjustment mechanism and drive mechanism. The mandrel 70 of the present embodiment does not require a support mandrel, though one may be used as shown in FIG. 7.

In FIG. 7, the mandrel 70 includes a right mandrel assembly 75a and a left mandrel assembly 75b. The left and right mandrel assemblies 75a, 75b include similar components as will be described below and referenced with the same reference numbers.

The left and right mandrel assemblies 75a, 75b each include a stent retaining fixture comprised of two components, a plurality of arms 72, 72' and a stent contacting member 73, 73' disposed between the two arms. The stent contacting member may be embodied in the form of a threaded member such as a piece of suture, or a metallic member such as a wire or other similar types of materials that may be disposed between the two arms 72, 72'. The stent contacting member 73, 73' may also be configured to be easily removed from the arms 72, 72', wherein the stent contacting member 73, 73' may be replaced after a process has been performed on the stent to reduce the possibility of contamination or failure. The arms 72, 72' are attached to a shaft member 71, 71' which is supported by a housing 74 as shown.

The right mandrel assembly 75a further includes a drive mechanism configured to provide rotational movement to the shaft member 71. Additionally, the shaft member 71 of the right mandrel assembly may further include an aperture disposed therethrough, wherein a support mandrel 13 may be disposed therethrough to aid in loading a stent between the two mandrel assemblies 75a, 75b.

The left mandrel assembly 75b further includes a drive mechanism coupled to the shaft member 71' and configured to provide rotational motion to the shaft member 71'. The left mandrel assembly 75b further includes a linear drive mechanism 77 coupled to the shaft member 71', wherein the linear drive mechanism is utilized to adjust the distance between the left mandrel assembly and the right mandrel assembly when stent 5 is placed between the two assemblies 75a, 75b. As shown in FIG. 7, the left mandrel assembly 75b may further include a biasing member 79, such as a spring, which acts on the shaft 71'. The biasing member 79 may act on the shaft 71' in combination with the linear drive member 77 or opposed to the linear drive member 77.

In use the stent 5 is placed between the left mandrel assembly 75b and the right mandrel assembly 75a, a support mandrel 13 is advanced through an aperture in the right mandrel assembly 75a and through the stent 5, wherein the distal end of the support mandrel 13 is received by the shaft 71' of the left mandrel assembly 75b. The distance between the two mandrel assemblies 75a, 75b is adjusted by moving the left mandrel assembly 75b, wherein the ends of the stent 5 are supported by the stent contacting members 73, 73'. The support mandrel 13 is then removed from the lumen of the stent and the right mandrel assembly 75a. Each of the rotational drive assemblies are then engaged to provide rotation to the mandrel assemblies and the stent. Preferably, the rotational drive assemblies are coupled together, thereby providing uniform rotational motion to the stent retained between the two mandrel assemblies.

It shall be understood that the arms 72, 72' and the stent contacting members 73, 73' may be replaced by any of the other mandrels in accordance with the above embodiments shown and described herein with reference to the present invention.

Although the mandrels and methods of use in accordance with the present invention have been described in accordance with stent coating, it will be understood by one of ordinary skill in the art that the mandrels in accordance with the present invention may be utilized for other purposes. For example, the mandrels may be utilized during electropolishing procedures, manufacturing procedures, storage or for similar purposes.

Referring again to FIGS. 1B and 1C, there is shown a stent holding device comprising a support mandrel 13 sized to fit in the lumen of a stent 5. Also shown is a plurality of stent retaining elements or fixtures 16, each including a character identifier 14. The character identifier can be a numeral (as shown), an alphabetic character, other readily recognizable symbol, or a combination thereof. The fixtures 16 are arranged longitudinally in series on the mandrel. The combination of identifiers 14 on the fixtures 16 provides a unique identifier for tracking a stent mounted on the stent holding device during a coating process or other manufacturing process. In the illustrated embodiment, the fixtures 16 provide the stent holding device with the numerical identifier of "21." Although three fixtures 16 are shown on the mandrel 13, any number fixtures may be used to provide a desired unique identifier. For example, if it is desired to assign a stent with the unique identifier "357A," four fixtures 16 can be arranged in series on the mandrel, with the first, second, third, and fourth fixtures having the identifiers of "3," "5," "7," and "A," respectively.

In addition to or as an alternative to a character identifiers, the fixtures 16 may include barcodes, other machine readable graphics, or RFID devices embedded in or mounted on the fixtures 16. The use of a character identifier, such as a numeral, has the advantage of being readily recognizable by persons handling the stent without the aid of barcode reading devices, RFID scanners, or other machines.

As shown in FIG. 1B, each of the plurality of stent retaining fixtures 16 includes a sloped surface 17 that protrudes from the main cylindrical body 18 of the fixture 16. The sloped surface 17 is conical and is sloped relative to a longitudinal axis 100 of the support mandrel 13. Although not visible in FIG. 1B, the second (middle) fixture 16 includes a tapered aperture shaped to receive the sloped surface 17 of the first fixture 16 located furthest away from the stent 5. Also, the third fixture 16, located closest to the stent 5, includes a tapered aperture 102 shaped to receive the sloped surface 17 of the second fixture 16. The tapered aperture 102 includes a conical recess portion that extends into the body 18 and a longitudinal bore that extends beneath the sloped surface 17. Preferably, the recess of the tapered aperture 102 has a shape that corresponds to the shape of the sloped surface 17 so as to allow adjacent fixtures 16 to matingly engage each other. The mandrel 13 extends through and frictionally engages the tapered aperture 102 of the fixtures 16. In this way, the fixtures 16 are prevented from inadvertently sliding off the mandrel 13.

The ability to add and remove fixtures 16 also facilitates mounting more than one stent on the stent holding device. For example, two fixtures 16 may be used to separate two stents disposed on the support mandrel 13. The two fixtures can be oriented in opposite directions such that their respective sloped surface faces toward and engages an adjacent stent edge.

Referring again to FIGS. 1E and 1F, there is shown a stent holding device comprising a support mandrel 13 including a segment sized to fit in the lumen of a stent 5. A fixture 30 is removably attached to an outer diameter of the mandrel 13. The fixture 30 includes a plurality of interconnected loop segments 110. The loop segments 110 are attached to the support mandrel. The loop segments 110 define an inner diameter 112 that is expandable from a first size to a second size. The first size is less than an outer diameter 114 of the support mandrel 13. The inner diameter 112 has the first size when the fixture 30 is removed from the support mandrel 13. The second size allows for a frictional fit between the loop segments 110 and the support mandrel 13. A frictional fit can be achieved with an inner diameter 112 that is equal in size to the outer diameter 114 of the mandrel 13. The inner diameter 112 has the second size when the fixture 30 is attached to the support mandrel 13, as shown in FIGS. 1E and 1F.

FIGS. 1E and 1F also show a tubular member 116 including a first end 31, a second end 32, and a spiral cut 33 formed in the tubular member. The spiral cut 33 extends from the first end 31 to the second end 32 such that the inner diameter 112 of the tubular member is expandable from the first size to the second size. The tubular member 116 can, for example, be formed of a flat spring or other resilient member that is coiled in a helical manner such that its inner diameter 112 tends to have the first size. The coiled spring of the tubular member 116 is configured such that twisting or longitudinally compressing the coiled spring forces the inner diameter to expand from the first size to the second size.

Referring once again to FIGS. 2 and 3, there is shown a stent holding device comprising a support mandrel 43 sized to fit in a stent lumen, and two Z-shaped fixtures 45 disposed on the mandrel 43 and spaced apart from each other by a distance selected to allow the fixtures to engage opposing end regions of a stent. Each of the fixtures 45 includes a first protruding portion 130 and a second protruding portion 132. The first protruding portion 132 extends in a radial direction 134 away from the support mandrel 43. The second protruding portion 134 extends in a different radial direction 136 from the support mandrel 43. The radial directions 134, 136 are opposite or 180 degrees from each other; however, the radial directions 134, 136 may be at other angles relative to each other. The first and second protruding portions 130, 132 define an outer diameter D of the fixture 45. The outer diameter D is sized such that the first and second protruding portions 130, 132 engage one or more luminal or inward facing surfaces of a stent lumen.

Referring again to FIG. 7, there is shown a stent holding apparatus 70 comprising a first region 140, a second end region 142 spaced apart from the first end region, a first stent retaining assembly or fixture 144 disposed at the first end region, and a second stent retaining fixture 146 disposed at the second end region. Each of the stent retaining fixtures 144, 146 includes two arms 72, 72' and a stent contacting member 73, 73' disposed between and attached to the two arms. The stent contacting member 73, 73' is formed of one or more filaments. Examples of a suitable filament include, without limitation, a suture, a metal wire, a threaded member, an elastic band, or a flexible pin. The stent contacting member 73, 73' can be removably attached to the ends of the arms in a manner that allows the stent contacting member 73, 73' to be detached and replaced whenever necessary.

The stent holding apparatus 70 optionally includes a support mandrel 13 sized to fit into a stent lumen and disposed between the first and second end regions 140, 142. In the illustrated embodiment, a portion of the support mandrel 13 extends from the first end region 140 and beyond the second end region 142. The support mandrel 13 is movable in longitudinal directions 150 through an aperture 148 formed in each of the fixtures 144, 146.

Still referring to FIG. 7, the first stent retaining fixture 144 is movable relative to the second end region 142, thereby allowing the first stent retaining fixture 144 to be moved closer or further from the second stent retaining fixture 146 as needed to allow for installation and removal of a stent and to accommodate and retain stents of differing sizes. The first stent retaining fixture is coupled to a biasing device 79 that urges the stent retaining fixture to a selected position relative to the second end region 142. An example of a suitable biasing device includes, without limitation, a spring.

In FIG. 7, the stent 5 is shown temporarily supported by the mandrel 13 prior to being supported by the stent contacting members 73, 73'. When the first stent retaining fixture 144 is linearly translated to the right, the stent 5 comes into contact with and is retained by the stent contacting members 73, 73'. Then, the mandrel 13 may be pulled out of the stent holding apparatus 70.

A linear drive mechanism 77, which can comprise gears 152, is coupled to the first stent retaining fixture 144 such that the fixture is translated linearly in a longitudinal direction when the linear drive mechanism is activated. A rotational drive mechanism 154 is coupled to the first and second stent retaining fixtures 144, 146 such that the stent retaining fixtures are rotated when the rotational drive mechanism is activated.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A stent holding apparatus, comprising:
   a first stent retaining element, the first stent retaining element comprising a first arm, a second arm extending away from the first arm, and a stent contacting member configured to contact and support a first end of a stent and having a length greater than an outer diameter of the stent at the first end of the stent, the stent contacting member disposed between and attached to the first and second arms; and
   a second stent retaining element, the second stent retaining element comprising a first arm, a second arm extending away from the first arm, and a stent contacting member configured to contact and support a second end of the stent opposite the first end and having a length greater than an outer diameter of the stent at the second end of the stent, the stent contacting member disposed between and attached to the first and second arms, and
   wherein the first end of the stent and second end of the stent are opposite ends of the stent.

2. The stent holding apparatus of claim 1, additionally including means for adjusting the distance between the first stent retaining element and the second stent retaining element for engaging and disengaging the stent between the first and second stent retaining elements.

3. The stent holding apparatus of claim 1, additionally comprising a tension adjustment mechanism to modify the tension applied to the stent by the first and second stent retaining elements.

4. The stent holding apparatus of claim 1, wherein the first stent retaining element is extending out of a first shaft member and the second stent retaining element is extending out of a second shaft member, the second shaft member having a hollow interior to allow a support mandrel to be inserted through the second shaft member and to be engaged with the first shaft member for assisting the positioning of a stent between the first stent retaining element and the second stent retaining element.

5. The stent holding apparatus of claim 1, wherein the first stent retaining element is movable relative to the second stent retaining element and is coupled to a biasing device that urges the first stent retaining element to a selected position relative to the second stent retaining element.

6. The stent holding apparatus of claim 1, wherein a first end of the first arm of the second stent retaining element converges toward a first end of the second arm of the second stent retaining element, and a second end of the first arm of the second stent retaining element diverges away from a second end of the second arm of the second stent retaining element.

7. The stent holding apparatus of claim 6, wherein the stent contacting member of the second stent retaining element is attached to the second end of the first arm of the second stent retaining element and to the second end of the second arm of the second stent retaining element.

8. The stent holding apparatus of claim 1, wherein a first end of the first arm of the first stent retaining element converges toward a first end of the second arm of the first stent retaining element, a second end of the first arm of the first stent retaining element diverges away from a second end of the second arm of the first stent retaining element, and the stent contacting member of the first stent retaining element is attached to the second end of the first arm of the first stent retaining element and to the second end of the second arm of the first stent retaining element.

9. The stent holding apparatus of claim 1, wherein the stent contacting member of the first stent retaining element is a first filament longer in length than the outer diameter of the stent at the first end of the stent, and the stent contacting member of the second stent retaining element is a second filament longer in length than the outer diameter of the stent at the second end of the stent.

10. The stent holding apparatus of claim 1, wherein the stent contacting member of the first stent retaining element and the stent contacting member of the second stent retaining element are arranged to hold the stent within in a space between the two stent contacting members.

11. The stent holding apparatus of claim 1, wherein the stent contacting members are removably attached to the arms.

* * * * *